(12) United States Patent
Gie et al.

(10) Patent No.: US 6,306,174 B1
(45) Date of Patent: Oct. 23, 2001

(54) FEMORAL COMPONENT

(75) Inventors: Graham Allan Gie, Yeoford; Robin Sydney Mackwood Ling, Dartmouth, both of (GB); John Andrew Storer, Bayeux (FR); Andrew John Timperley, Exeter (GB)

(73) Assignee: Benoist Girard SAS (FR)

( * ) Notice: Subject to any disclaimer, the term of this patent is extended or adjusted under 35 U.S.C. 154(b) by 0 days.

(21) Appl. No.: 09/464,580

(22) Filed: Dec. 16, 1999

(30) Foreign Application Priority Data

Dec. 18, 1998 (GB) .................................................. 9828084
Dec. 18, 1998 (GB) .................................................. 9828085

(51) Int. Cl.$^7$ .................................................... A61F 2/36
(52) U.S. Cl. ................................... 623/22.42; 623/23.15; 623/23.47
(58) Field of Search ............................ 623/23.15, 22.41, 623/22.42, 22.43, 22.45, 22.46, 23.14, 23.18, 23.21, 23.23, 23.25, 23.47, 22.12

(56) References Cited

U.S. PATENT DOCUMENTS

| | | | | |
|---|---|---|---|---|
| 3,067,740 | * | 12/1962 | Haboush ................................ | 623/23 |
| 4,051,559 | | 10/1977 | Pifferi ................................... | 623/22 |
| 5,002,578 | * | 3/1991 | Luman ................................... | 623/23 |
| 5,201,882 | * | 4/1993 | Paxson .................................. | 623/23 |
| 5,286,260 | * | 2/1994 | Bolesky et al. ........................ | 623/23 |
| 5,702,479 | * | 12/1997 | Schawalder ............................ | 623/23 |
| 5,858,020 | * | 1/1999 | Johnson et al. ........................ | 623/23 |
| 5,931,871 | | 8/1999 | Baur et al. ............................. | 623/23 |
| 6,083,263 | * | 7/2000 | Draenert et al. ....................... | 623/23 |

FOREIGN PATENT DOCUMENTS 1 409 054    10/1975   (GB) .

* cited by examiner

*Primary Examiner*—Bruce Snow
(74) *Attorney, Agent, or Firm*—Lerner, David, Littenberg, Krumholz & Mentlik, LLP

(57) ABSTRACT

A femoral component of a replacement hip joint is provided which has a stem for fixing in cement in a medullary cavity by cement and having a separate proximal component provided with a neck for a ball head. An attachment system is provided for securing the proximal component to the stem which allows selection of an infinite number of angularly displaced positions about a proximal/distal axis, and adapted to allow fixation of the two parts after insertion of the stem into the prepared medullary cavity and without causing torsional loads on the stem. The stem extends proximally to the level of the bone cut which allows the proximal component to rotate after the stem is implanted. If an infinite number of angularly displaced positions is not required, then a Vernier coupling system with a large member of positions can be used.

24 Claims, 6 Drawing Sheets

FEMORAL COMPONENT

BACKGROUND OF THE INVENTION

1. Field of the invention

This invention related to a femoral component of a replacement hip joint of the "Exeter" type which has a collarless stem including a shoulder for fixing in a medullary canal by cement.

2. Discussion of Prior Art

The "Exeter" type femoral component of the kind shown in British Patent No. 1 409 054 is well known and comprises a neck which carries a ball head for cooperation with an acetabular socket. The neck is connected to a tapered collarless stem. Thus, there is no collar for resting either on the bone or the cement in the area where the stem joins the neck of the implant. This type of stem has evolved so that the stem can be given a highly polished finish to help it slide down inside the bone cement and the present invention relates to this type of femoral component.

In certain circumstances, it can be difficult to locate the femoral component in the medullary socket with the neck and ball at the precise height and angle required. This can be caused by the bone which are structurally imperfect or by difficulties in reaming a suitable cavity. It is particularly pronounced when cavities have to be lined with bone fragments prior to cementing or when there are irregularities and the present invention is intended to overcome some of the difficulties experienced.

It is known from U.S. Pat. No. 5,931,871 to provide a femoral component with a separate proximal component but in this application, the angle of the proximal component with regard to the stem about a proximal/distal axis is fixed and there is no provision for adjustment.

U.S. Pat. No. 4,051,559 also shows the use of a separate proximal component and this is provided to allow it to be placed in position on a cylindrical stem which is intended to be screwed directly into the bone. The proximal component is provided with a collar which is intended to rest against the cut and prepared bone and there is no provision for a stem to slide down inside bone cement as is required by the Exeter type hip stem. Moreover, the angular adjustment about a proximal/distal axis may be too coarse to allow final accurate adjustment with an Exeter type component.

SUMMARY OF THE INVENTION

According to the present invention, a femoral component of a replacement hip joint has a stem for fixing in cement in a medullary cavity by cement and having a separate proximal component provided with a neck for a ball head, and including an attachment system for securing the proximal component to the stem which allows selection of an infinite number of angularly displaced positions about a proximal/distal axis, and adapted to allow fixation of the two parts after insertion of the stem into the prepared medullary cavity and causing minimal torsional loads on the stem. The stem extends proximally to the level of the bone cut which allows the proximal component to rotate after the stem is implanted. The attachment system includes a vernier coupling.

Thus, with the component according to the present invention, it is possible to insert the stem into a prepared medullary cavity and subsequently add the proximal component at the precise angle about the proximal/distal axis and then complete fixation of the two parts without causing torsional loads on the stem which might cause the stem to move in the cement and create cavities or cause other damage. This also prevents the stem from being twisted about the proximal/distal axis which might alter the precisely prepared angle of the proximal component.

If an infinite number of positions is unnecessary, the use of a Vernier coupling in the attachment system enables a very large number of positions to be used and provides a simple and inexpensive method of manufacture. In one preferred embodiment, the boss and cavity are tapered and in another they are cylindrical.

Preferably, the attachment system include a male element on the stem adapted to cooperate with the female structure on the proximal component. Thus, the male element may comprise a boss on the proximal portion of the stem and the female structure can be provided by a cavity to receive and cooperate with the boss, and a release or locking element can be provided for preventing axial movement after initial fixing.

In one embodiment, the boss can be tapered to engage a tapered cavity on the proximal component and the release element may comprise an axially extending locking screw extending from the proximal component into the tapered boss.

Alternatively, the release or locking element may comprise a cotter pin adapted to locate on a boss extension, the pin extending tangentially to the extension.

In another construction, the release can be provided by a circumferential groove in the boss which can be engaged by a radially extending lock pin or screw in the proximal component.

According to another preferred construction, the boss can be cylindrical and with this arrangement, the release element can again be provided by a tangentially extending cotter pin located in the proximal component. If desired, the cotter pin can be located in a groove in the boss.

With these arrangements, the release element may comprise a radially extending pin or screw in the proximal component which can engage a peripheral groove in the boss.

In another alternative construction, the boss can be cylindrical or tapered and be provided with a peripheral groove and the release element can comprise a locking plate with means to move it radially to engage said groove. The corresponding cavity is also cylindrical or tapered to match the boss.

In yet another embodiment, the proximal member and stem can each be provided with a predetermined number of openings arranged at the same radius about an axis substantially parallel to the long axis of the prosthesis, one ring of openings having one more opening than the other, and a locking member adapted to enter one of each ring of holes to provide a Vernier coupling. Thus, one ring of holes can be provided in the male element and the other in the proximal component.

BRIEF DESCRIPTION OF THE DRAWINGS

The invention can be performed in many ways and some embodiments will now be described by way of example and with reference to the accompanying drawings in which.

DESCRIPTION OF THE PREFERRED EMBODIMENTS

As shown in the drawing, the femoral component comprises two parts, a shoulderless stem 1 and a proximal component 2. The proximal component has an engagement portion 3 and a neck 4 with a tapered spigot 5 to receive a ball head 6.

The portion 3 is provided with a tapered cavity 7 which is adapted to cooperate with a tapered boss 8 provided on the proximal end of the stem 1. The taper can be a morse taper so that when pressed together the two parts tend to lock in position.

Figure 1:
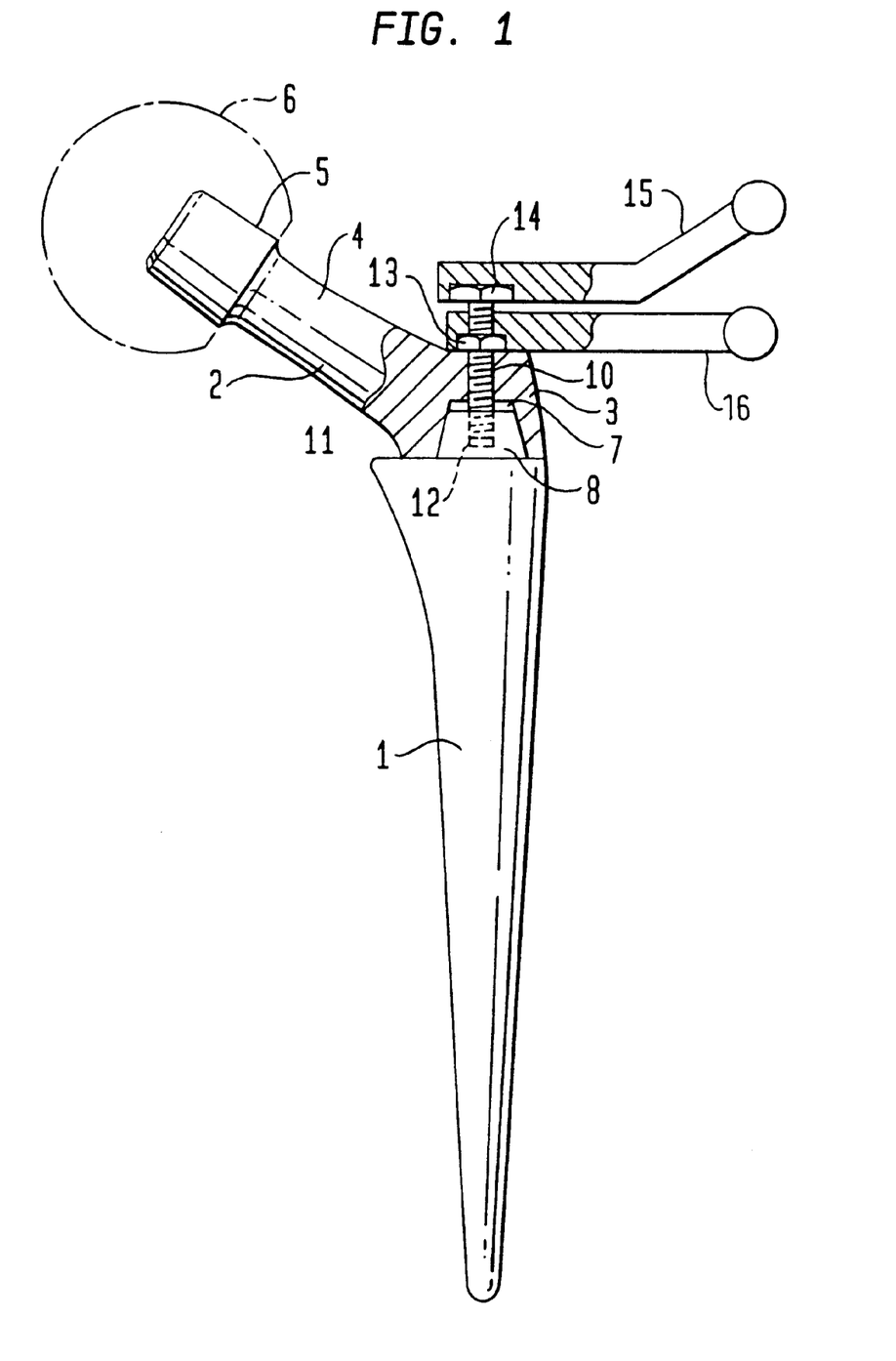
FIG. 1 is a part cross-sectional diagrammatic side elevation of a femoral component using a collarless stem for fixing in cement in a medullary cavity according to the present invention.

In order to prevent the taper inadvertently coming apart during use an attachment system is provided which, in FIG. 1, comprise a screw 10 which extends through an opening 11 in the proximal component and passes into a threaded bore 12 in the tapered boss 8. The screw 10 carries a lock nut 13 and has a hexagonal, or other appropriately shaped head 14. In order to tighten and lock screw 10, two especially shaped spanners 15 and 16 are provided.

In order to insert the femoral component according to the invention, the medullary cavity of the bone to which it is to be fitted is suitably prepared and lined with cement. The stem 1 is now inserted, perhaps using an appropriate inserter, but due to the construction of the present invention, its angular position about a proximal/distal axis is not vital and it can therefore be inserted so that it can take up the best and appropriate position in the cavity. Thus, it can be positioned so that it has the maximum amount of cement about it so that it is riot close to any of the cavity walls.

With the stem located in the cavity, the proximal component can be carefully fitted so that it projects angularly about the proximal/distal axis as is required. In order to hold the tapers in position it may be necessary to deliver a light blow in the proximal/distal axis direction to ensure that the tapers seat and grip.

In order to prevent inadvertent release of the tapers, the screw 10 is now inserted to a marked position where it is known that there is sufficient thread within the boss 8. The locking screw 13 is now initially gently tightened down by hand and the spanner wrenches 15 and 16 are now employed to ensure that the screw 10 between the tapered boss 8 and the top of the portion 3 is pulled up tightly to again ensure that the tapers hold. In order to do this, the spanner 15 is used to hold the screw head 14 and prevent rotation and the spanner is employed to tighten the nut 13. Due to the juxtaposition of the spanners this can be achieved without applying any torsion to the stem 1 and thus prevents inadvertent movement of the possibility of loosening the stem in the rapidly drying cement.

The spanners are, of course, removed after the femoral component and the stem have been locked together. The screw may be removed, as required, without altering the engagement of the tapers.

Figure 2:
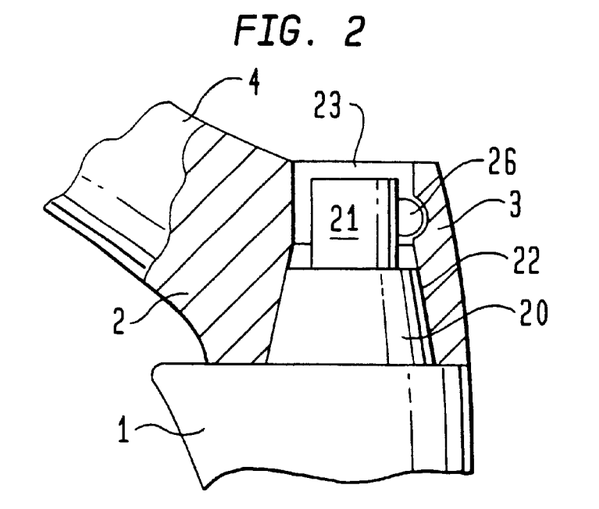
FIG. 2 is a part cross-sectional part view of an alternative embodiment.
Figure 3:
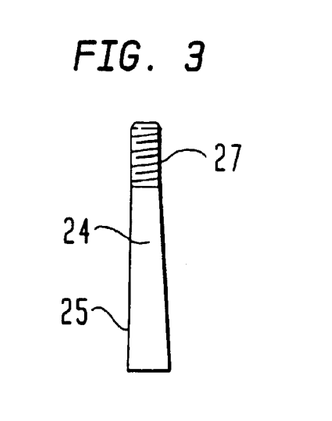
FIG. 3 is a side elevation of a cotter pin for use in the embodiment shown in FIG. 2.

FIGS. 2 and 3 show an alternative construction again using a tapered boss and the same reference numerals are used to indicate similar parts as in FIG. 1. In the construction, the tapered boss is indicated by reference numeral 20 and has a cylindrical extension 21. The proximal component 2 is again provided with a tapered socket 22 which in this construction extends upwardly as a cylindrical opening 23.

In this construction, the releasable means includes a cotter pin 24 as shown in FIG. 3. This cotter pin has a flat side 25 and is shaped to pass through a hole 26 provided in the portion 3 and shaped so that the flat side of the tapered pin 24 engages the cylindrical extension 21, the flat side being tangential to the extension.

The stem is inserted as described with regard to FIG. 1 and the proximal component again placed in position. In order to locate the proximal component in place, the cotter pin is inserted through the opening 26 and tightened by a nut (not shown) on a threaded portion 27. This pulls the cotter pin through on its taper firmly engaging it with the extension 21. Once again, it will be seen that no torsional twisting movement is applied to the stem 1 as the releasable locking means are placed in position.

Figure 4:
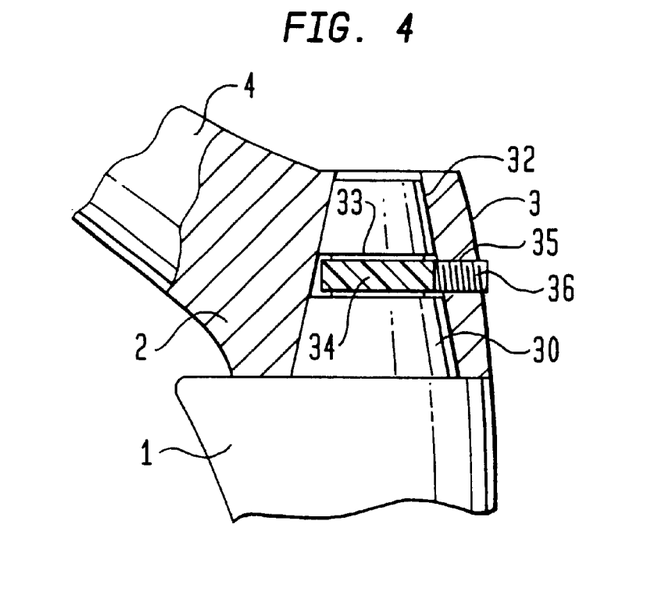
FIG. 4 is a part cross-sectional side elevation of another alternative embodiment.

In FIG. 4, the same reference numerals are again used to indicate similar part to those shown in FIG. 1 but in this construction an extended tapered boss 30 is used and the socket 32 extends through the portion 3. The tapered boss 30 has a groove 33 which is lined with a bonded synthetic plastics material indicated by reference numeral 34. The portion 3 has a threaded opening 35 to receive a set screw 36.

With this embodiment, the parts are again assembled together in the manner described with regard to the previous figures and the releasable locking system is provided by tightening the screw 36 which extends substantially radially to the proximal/distal axis.

Figure 5:
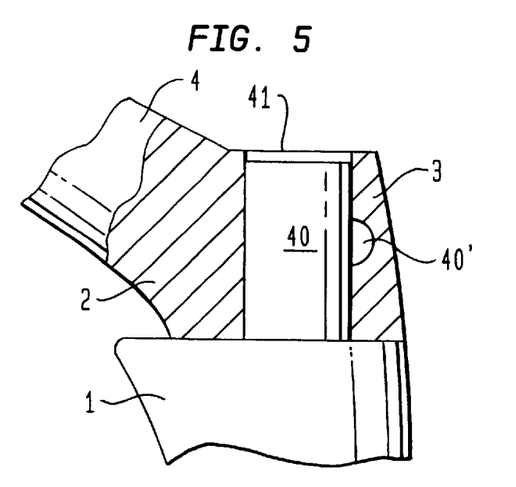
FIG. 5 is a part cross-sectional side elevation of another alternative embodiment using a cylindrical boss.
Figure 6:
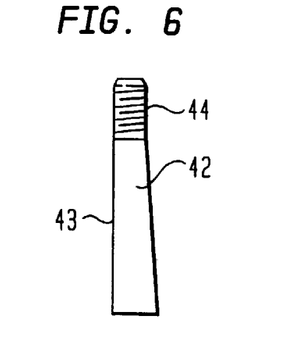
FIG. 6 is a side elevation of a cotter pin for use with the embodiment shown in FIG. 5.

FIGS. 5 and 6 show another embodiment according to the invention in which the same reference numerals are again used as those employed in FIG. 1 to indicate similar parts but in this construction the tapered boss of FIGS. 1 and 4 is replaced by a cylindrical boss 40 which extends through an open socket 41 in the proximal component. A cotter pin 42 is again employed, this having a flat side 43 and a threaded end 44. The portion 3 is provided with a suitably shaped opening 40' to receive the pin which is inserted and locking in position in a similar manner to that described with regard to FIG. 2.

Figure 7:
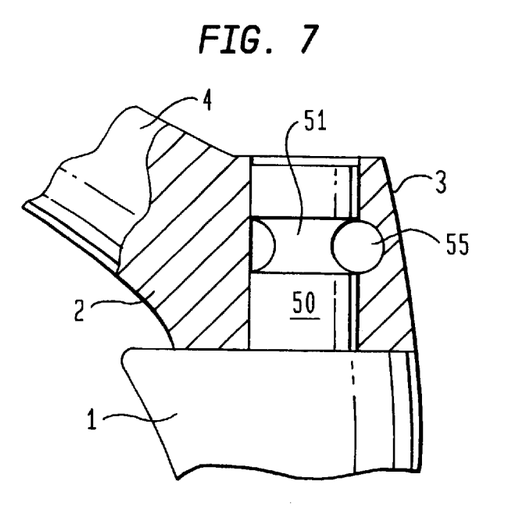
FIG. 7 is a part cross-sectional side elevation of yet another alternative embodiment.
Figure 8:
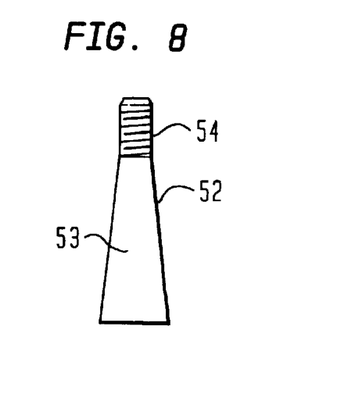
FIG. 8 is a side elevation of a cotter pin for use in the embodiment shown in FIG. 7.

FIGS. 7 and 8 also show a construction in which a cotter pin is used but in this arrangement the cylindrical boss 50 is provided with a peripheral groove 51 into which a tapered cotter pin 52 can extend. The cotter pin has a cylindrical tapered shank 53 and is provided with a threaded end 54. The pin is passed through an opening 55 in the portion 3, one side of the pin engaging the opening 55 and the other engaging in the groove 51. Once again, it is locked in position by means of a screw on the thread 54.

Figure 9:
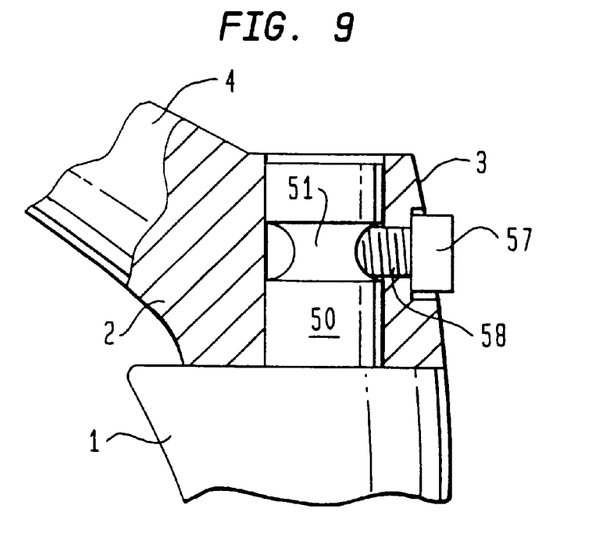
FIG. 9 is another part cross-sectional side elevation of another alternative embodiment.

FIG. 9 shows another construction using a boss with a groove 51 similar to that shown in FIG. 7 but in this construction the cotter pin is replaced by a locking screw 57 which engages the groove by passing through a threaded opening 58 in the portion 3.

Figure 10:
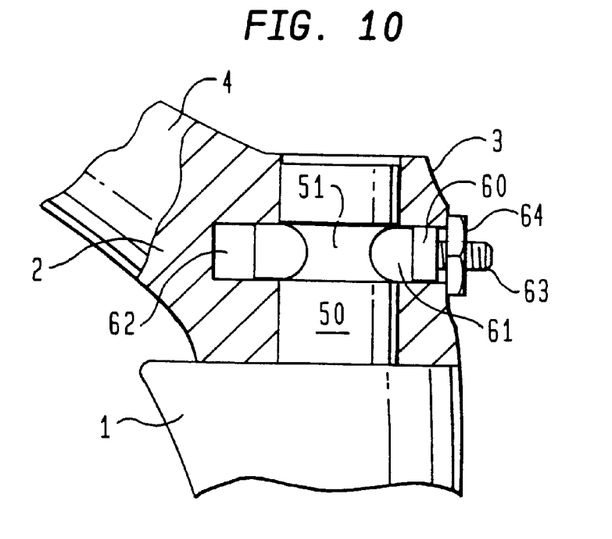
FIG. 10 is a part cross-sectional side elevation of yet a further alternative embodiment.
Figure 11:
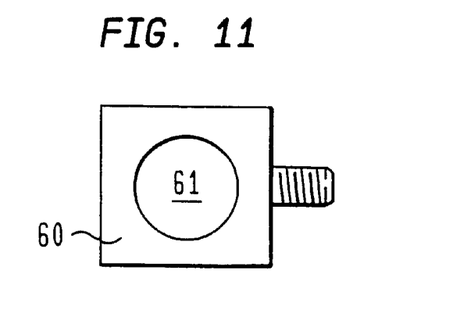
FIG. 11 is a plan view of a locking plate for use in the construction shown in FIG. 10.

FIGS. 10 and 11 show another construction in which a boss 50 is provided with a groove 51 but the screw 57 of FIG. 9 is replaced by a locking plate 60. This plate 60 has a central opening 61 and is located in a slot 62 in the portion 3. The plate is provided with a projecting screw 63 on which is located a tightening nut 64. It will be seen from FIG. 1 that the inner edges of the opening 61 are bevelled to accurately locate in the groove 51.

In order to operate this arrangement, the plate is located in position in the slot 62 before the proximal component is placed on the boss 50, the angular position is carefully located and the boss is held in position by tightening up the nut 64 which pulls the plate into a position where it can lock against the groove 51.

It will be appreciated that in all constructions described above, it is possible to lock the two parts together without creating a torsional twisting movement to the stem 1.

Figure 12:
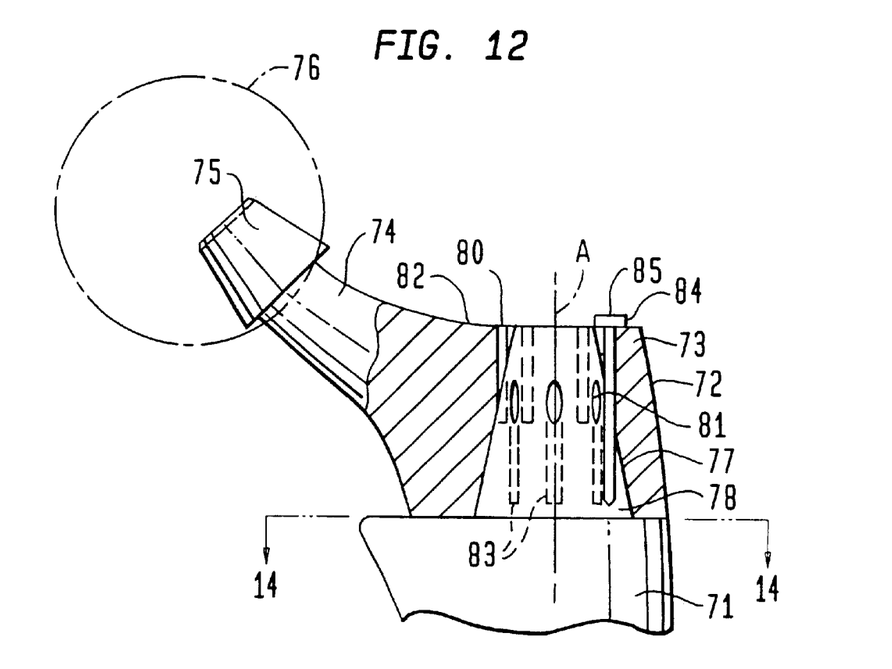
FIG. 12 is a diagrammatic part cross-sectional side elevation of a femoral component according to the invention.
Figure 13:
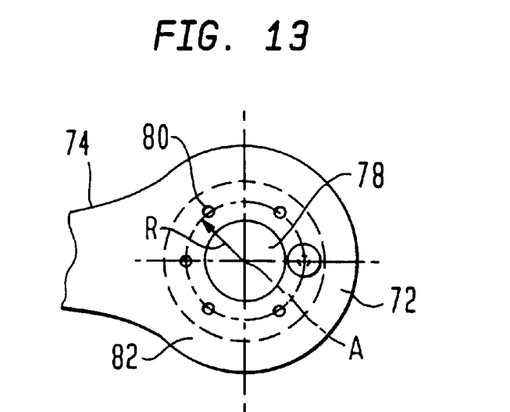
FIG. 13 is a partial plan view of the construction shown in FIG. 12.
Figure 14:
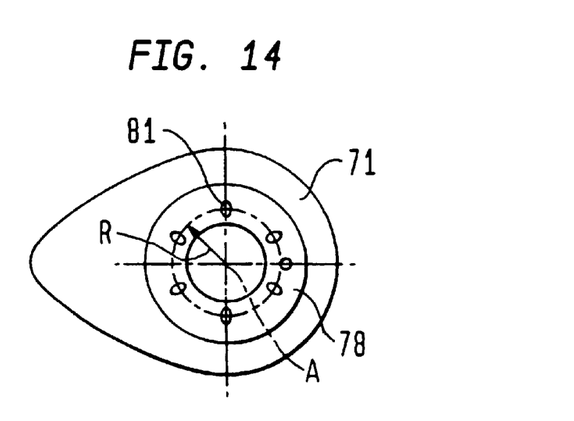
FIG. 14 is a plan view on the line 14—14 of FIG. 12.

As shown in FIGS. 12–14, the femoral component according to the invention comprises a Vernier coupling provided by a ring of openings 80 in a proximal component 72. The openings 80 are arranged on a radius r about a proximal/distal axis A.

A second ring of openings 81 are provided on a stem 71 and are arranged on the same radius r about the same axis A as the openings 80 in the proximal component. These openings 81 extend into the wall of a boss 78 whilst the openings 80 are arranged to open through a proximal surface 82 of the proximal component surrounding the open end of a tapered cavity 77. As will be seen from FIG. 12, the distal end of the openings 80 extend into the tapered cavity 72 at a position in line with the proximal ends of the openings 81 in the boss and the distal end 83 of each of the openings 81 is towards the distal end of the boss.

A locating pin 84 having a head 85 is provided which is a push or tight fit in the openings 81. In an alternative embodiment (not shown) the openings 81 are threaded and the pin 84 is replaced by a screw which can engage the thread.

The Vernier effect is created in the construction shown in FIG. 12 by providing six openings 80 and seven openings 81. This allows small increments of angular adjustment between the proximal component and the stem 71.

If desired, more accuracy of adjustment can be arranged by providing more openings 80 and 81 but only six and seven respectively have been shown in the drawings so that they are clear.

If a pin 84 is used, then any pressure placed on the femoral component is in direction of the proximal/distal axis. If a screw is used, then any torsional twisting movement of the stem when the proximal component is fitted need only be very light.

In order to fit the femoral component, a medullary cavity is prepared in the usual way and the stem 1 is first inserted, being allowed to take up any angular position about a proximal/distal axis as is desired by the surgeon, thus enabling the maximum cement mantle to be achieved. The proximal component is now fitted and the correct angle assessed by the surgeon, the very small increments of angular movement allowing good accuracy. The pin 84 or screw can be lightly inserted and then the femoral component tapped or have pressure applied to ensure that the taper between the boss and the cavity locks. The pin or screw 84 is now driven fully home thus ensuring that the proximal component and the stem are firmly locked together.

Figure 15:
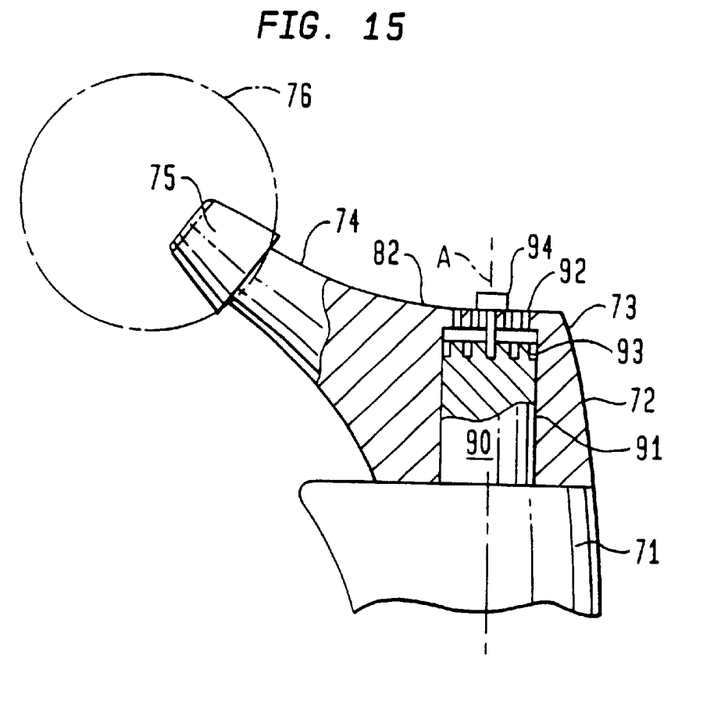
FIG. 15 is a view similar to FIG. 12 of an alternative embodiment.

An alternative embodiment is shown in FIG. 15 and the same reference numerals are used to indicate similar parts. In this arrangement however a cylindrical boss 90 is employed on the stem 71 and is a close sliding fit in a cylindrical cavity 91 in the proximal component 72. The end of the cavity 91 is closed and the end wall is provided with a ring of openings 92 which are again around a fixed radius based on a proximal/distal axis A. A further ring of openings 93 are provided in the proximal end of the boss 90 which are again on the same radius and about the same axis A. Once again there is one more hole 93 than holes 92 and a Vernier coupling is provided by the insertion of a pin or screw 94 into an appropriate pair of mating holes at the desired angular position.

Figure 16:
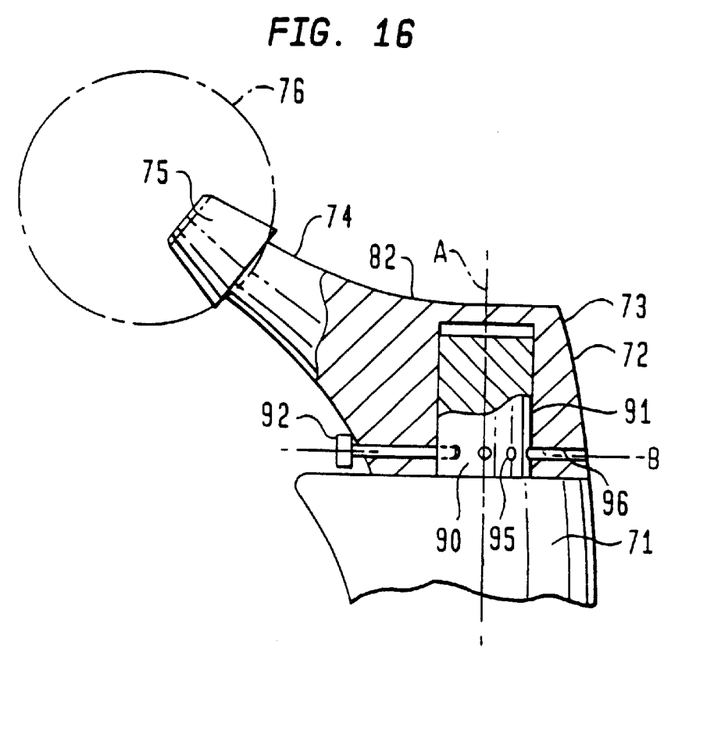
FIG. 16 is a view similar to FIG. 15 of yet another alternative embodiment.

FIG. 16 shows another alternative construction again employing the same reference numerals to indicate similar parts. In this construction a cylindrical boss 90 is again shown but this carries a ring of blind openings 95 which are aligned in a plane B with a second ring of openings 96 provided in the proximal component 72. There are six openings 95 and seven openings 96 and a pin or screw 97 is provided to achieve the Vernier coupling. This arrangement could also be employed with a tapered boss and cavity of the kind shown in FIG. 12.

What is claimed is:

1. The femoral component of a replacement hip joint comprising: a stem for fixing in cement in a medullary cavity and a separate proximal component which has a neck for a ball head, and an attachment element for securing said proximal component to the stem which allows the selection of a number of angularly displaced positions about a proximal/distal axis and adapted to allow fixation of the two parts after insertion of the stem into the medullary cavity causing minimal torsional loads on said stem, said attachment element including a Vernier coupling.

2. The femoral component as claimed in claim 1 in which said attachment element includes a male element on said stem adapted to cooperate with a female structure on the proximal component.

3. The femoral component as claimed in claim 2 in which said male element comprises a boss on the proximal part of said stem and said female structure can be provided by a cooperating cavity to receive the boss.

4. The femoral component as claimed in claim 3 in which said boss and said cavity are tapered.

5. The femoral component as claimed in claim 3 in which said boss and said cavity are cylindrical.

6. The femoral component as claimed in claim 3 in which said proximal member and said stem are each provided with a predetermined number of openings arranged at the same radius about an axis substantially parallel to the long axis of the prosthesis, one ring of openings having one more opening than the other and a locking member adapted to enter one of each ring of holes to provide a Vernier coupling.

7. The femoral component as claimed in claim 6 in which one ring of holes is provided in the male element and the other in the proximal component.

8. A femoral component as claimed in claim 1 in which said proximal member and said stem are each provided with a predetermined number of openings arranged at the same radius about an axis substantially parallel to the long axis of the prosthesis, one ring of openings having one more opening than the other and a locking member adapted to enter one of each ring of holes to provide a Vernier coupling.

9. A femoral component for a replacement hip joint having a stem for implantation into the medullary cavity comprising:

- a trunnion extending from a proximal portion of said stem, said trunnion having a plurality of recesses formed therein;
- a neck portion having a cavity for rotatably receiving said trunnion;
- a locking element insertable into at least one of said plurality of recesses in said trunnion, said locking element engageable with said neck portion to prevent the rotation of said trunnion with respect to said neck.

10. The femoral component as set forth in claim 9 wherein the trunnion is tapered and said cavity in said neck has a mating taper.

11. The femoral component as set forth in claim 10 wherein the trunnion has a locking Morse taper.

12. The femoral component as set forth in claim 9 wherein the locking element is a pin.

13. The femoral component as set forth in claim 12 wherein the pin is inserted into the neck portion and into the trunnion in a generally proximal-distal direction.

14. The femoral component as set forth in claim 12 wherein the pin is inserted into the neck portion in a direction generally perpendicular to the proximal-distal direction.

15. The femoral component as set forth in claim 9 wherein the recesses in the trunnion are bores extending in a generally proximal-distal direction.

16. The femoral component as set forth in claim 15 wherein said bores are aligned with corresponding bores in said neck portions.

17. The femoral component as set forth in claim 16 wherein the locking element is a pin.

18. The femoral component as set forth in claim 17 wherein the pin is inserted into the neck portion and into the trunnion in a generally proximal-distal direction.

19. The femoral component as set forth in claim 9 wherein the trunnion is cylindrical and the cavity in the neck ion is a bore for slidably engaging said trunnion.

20. The femoral component as set forth in claim 19 wherein the locking element is a pin.

21. The femoral component as set forth in claim 19 wherein the pin is inserted into the neck portion in a direction generally perpendicular to the proximal-distal direction.

22. The femoral component as set forth in claim 21 wherein the recesses in the trunnion are bores extending in a generally proximal-distal direction.

23. The femoral component as set forth in claim 22 wherein said bores are aligned with corresponding bores in said neck portions.

24. The femoral component as set forth in claim 23 wherein said bores form a ring around said neck portion and said trunnion.

* * * * *

UNITED STATES PATENT AND TRADEMARK OFFICE
CERTIFICATE OF CORRECTION

PATENT NO. : 6,306,174 B1  Page 1 of 1
DATED : October 23, 2001
INVENTOR(S) : Graham A. Gie, Robin S. Ling, John A. Storer and Andrew J. Timperley It is certified that error appears in the above-identified patent and that said Letters Patent is hereby corrected as shown below:

<u>Title page,</u>
Item [75], Inventor, before Exeter insert -- St. Leonard's --.

<u>Column 3,</u>
Line 59, "riot" should read -- not --.

<u>Column 8,</u>
Line 14, "ion" should read -- portion --.
Line 18, "19" should read -- 20 --.

Signed and Sealed this

Twenty-eighth Day of May, 2002

*Attest:*

JAMES E. ROGAN
*Attesting Officer*   *Director of the United States Patent and Trademark Office*